United States Patent
Orbay et al.

(10) Patent No.: US 7,727,264 B2
(45) Date of Patent: *Jun. 1, 2010

(54) INTRAMEDULLARY FIXATION DEVICE FOR METAPHYSEAL LONG BONE FRACTURES

(75) Inventors: Jorge L. Orbay, Miami, FL (US); Javier E. Castañeda, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/515,699

(22) PCT Filed: May 9, 2003

(86) PCT No.: PCT/US03/14775

§ 371 (c)(1),
(2), (4) Date: Nov. 25, 2005

(87) PCT Pub. No.: WO03/101320

PCT Pub. Date: Dec. 11, 2003

(65) Prior Publication Data

US 2006/0100624 A1    May 11, 2006

Related U.S. Application Data

(63) Continuation-in-part of application No. 10/315,787, filed on Dec. 10, 2002, now Pat. No. 6,706,046, which is a continuation-in-part of application No. 10/159,611, filed on May 30, 2002, now Pat. No. 6,730,090.

(51) Int. Cl.
*A61B 17/80* (2006.01)
(52) U.S. Cl. .................................... 606/280
(58) Field of Classification Search ............ 606/62, 606/63, 64, 65, 66, 67, 68, 69, 70, 71
See application file for complete search history.

(56) References Cited

U.S. PATENT DOCUMENTS 388,000 A    8/1888    Rider (Continued)

FOREIGN PATENT DOCUMENTS

CA    2174293 A    10/1997

(Continued)

OTHER PUBLICATIONS

"Advances in distal Radius Fracture Management (D)", transcript of American Academy of Orthopaedic Surgeons 2001 Conf.; pp. 134-151, Feb. 28, 2001 including Article by Matthew D. Putnam MD, "Repair and Rehabilitation of Distal Fractures: The Role of Subchondral Fixation" at pp. 144-147.

(Continued)

*Primary Examiner*—Thomas C Barrett
*Assistant Examiner*—Nicholas Woodall

(57) ABSTRACT

A fixation system (10) includes a device having a nail portion (12) and a plate portion (14), preferably horizontally and vertically offset relative to the nail portion by a neck portion (16). The nail portion (12) includes preferably threaded screw holes (24, 26), and the plate portion (14) includes longitudinally displaced peg holes (50, 52, 54), each of which is adapted to orient a peg (56, 58, 60) in a different orientation from the others. The system (10) also includes unicortical screws (28) having a reasonably large head (36) adapted to seat against the outer surface of the bone and a threaded shaft (32) adapted to engage in the screw holes (24, 26), and pegs (56, 58, 60) adapted to engage in the peg holes (50, 52, 54). Where threaded screw holes (24, 26) are used, bone is clamped between the nail portion (12) and the head (36) of the unicortical screws (28, 30). The pegs (56, 58, 60) provide stabilization and support for subchondral fragments. Moreover, as the pegs (56, 58, 60) preferably enter the subchondral fragments from a plurality of directions, additional fixation of the device (10) into the bone is provided.

16 Claims, 6 Drawing Sheets

U.S. PATENT DOCUMENTS

| | | | |
|---|---|---|---|
| 472,913 A | 4/1892 | Taylor | |
| 1,151,861 A | 8/1915 | Brumback | |
| 2,056,688 A | 10/1936 | Peterka et al. | |
| 2,500,370 A | 3/1950 | McKibbin | |
| 2,526,959 A | 10/1950 | Lorenzo | |
| 2,821,979 A | 2/1958 | Cameron | |
| 3,025,853 A | 3/1962 | Mason | 128/92 |
| 3,236,141 A | 2/1966 | Smith | 85/45 |
| 3,645,161 A | 2/1972 | Wesker | |
| 3,709,218 A * | 1/1973 | Halloran | 606/64 |
| 3,717,146 A | 2/1973 | Halloran | |
| 3,741,205 A * | 6/1973 | Markolf et al. | 606/61 |
| 3,842,825 A | 10/1974 | Wagner | |
| 3,939,498 A | 2/1976 | Lee et al. | 3/1.913 |
| RE28,841 E | 6/1976 | Allgower et al. | |
| 4,011,863 A * | 3/1977 | Zickel | 606/299 |
| 4,119,092 A | 10/1978 | Gil | |
| 4,135,507 A | 1/1979 | Harris | 128/92 |
| 4,153,953 A | 5/1979 | Grobbelaar | 3/1.913 |
| 4,169,470 A * | 10/1979 | Ender et al. | 606/62 |
| 4,172,452 A | 10/1979 | Forte et al. | 128/923 |
| 4,408,601 A | 10/1983 | Wenk | |
| 4,467,793 A * | 8/1984 | Ender | 606/62 |
| 4,473,069 A * | 9/1984 | Kolmert | 606/64 |
| 4,483,335 A | 11/1984 | Tornier | 128/92 |
| 4,484,570 A | 11/1984 | Sutter et al. | |
| 4,488,543 A | 12/1984 | Tornier | |
| 4,493,317 A | 1/1985 | Klaue | |
| 4,503,847 A * | 3/1985 | Mouradian | 606/64 |
| 4,506,662 A | 3/1985 | Anapliotis | 128/92 |
| 4,565,193 A | 1/1986 | Streli | |
| 4,622,959 A * | 11/1986 | Marcus | 606/64 |
| 4,651,724 A | 3/1987 | Berentey et al. | |
| 4,712,541 A * | 12/1987 | Harder et al. | 606/67 |
| 4,733,654 A | 3/1988 | Marino | 606/64 |
| 4,776,330 A | 10/1988 | Chapman et al. | 128/92 |
| 4,790,302 A | 12/1988 | Colwill et al. | |
| 4,794,919 A * | 1/1989 | Nilsson | 606/65 |
| 4,800,874 A | 1/1989 | David et al. | |
| 4,867,144 A | 9/1989 | Kara et al. | |
| 4,915,092 A * | 4/1990 | Firica et al. | 606/67 |
| 4,923,471 A | 5/1990 | Morgan | 923/16 |
| 4,955,886 A | 9/1990 | Pawluk | |
| 5,006,120 A | 4/1991 | Carter | |
| 5,013,314 A | 5/1991 | Firica et al. | 606/64 |
| 5,015,248 A | 5/1991 | Burstein et al. | |
| 5,035,697 A | 7/1991 | Frigg | 606/67 |
| 5,041,113 A | 8/1991 | Biedermann et al. | |
| 5,057,110 A | 10/1991 | Kranz et al. | |
| 5,085,660 A | 2/1992 | Lin | |
| 5,127,912 A | 7/1992 | Ray et al. | |
| 5,151,103 A | 9/1992 | Tepic et al. | |
| 5,190,544 A | 3/1993 | Chapman et al. | |
| 5,197,966 A * | 3/1993 | Sommerkamp | 606/69 |
| 5,201,733 A | 4/1993 | Etheredge, III | |
| 5,275,601 A | 1/1994 | Gogolewski et al. | |
| 5,304,180 A | 4/1994 | Slocum | 606/69 |
| 5,352,228 A | 10/1994 | Kummer et al. | |
| 5,352,229 A | 10/1994 | Goble et al. | 606/72 |
| 5,356,253 A | 10/1994 | Whitesell | |
| 5,356,410 A * | 10/1994 | Pennig | 606/62 |
| 5,364,399 A | 11/1994 | Lowery et al. | |
| 5,382,248 A | 1/1995 | Jacobson et al. | 606/60 |
| 5,437,667 A | 8/1995 | Papierski et al. | |
| 5,443,466 A * | 8/1995 | Shah | 606/62 |
| 5,458,654 A | 10/1995 | Tepic | 623/23 |
| 5,472,444 A | 12/1995 | Huebner et al. | 606/64 |
| 5,484,438 A | 1/1996 | Pennig | 606/64 |
| 5,486,176 A | 1/1996 | Hildebrand et al. | |
| 5,527,311 A | 6/1996 | Procter et al. | |
| 5,531,745 A | 7/1996 | Ray | |
| 5,531,746 A | 7/1996 | Errico et al. | |
| 5,536,127 A | 7/1996 | Penig | 411/413 |
| 5,549,612 A | 8/1996 | Yapp et al. | |
| 5,558,674 A | 9/1996 | Heggeness et al. | |
| 5,578,035 A | 11/1996 | Lin | 606/68 |
| 5,586,985 A | 12/1996 | Putnam et al. | |
| 5,591,168 A | 1/1997 | Judet et al. | 606/65 |
| 5,601,553 A | 2/1997 | Trebing et al. | |
| 5,603,715 A * | 2/1997 | Kessler | 606/63 |
| 5,607,426 A | 3/1997 | Ralph et al. | |
| 5,662,655 A | 9/1997 | Laboureau et al. | 606/75 |
| 5,665,086 A * | 9/1997 | Itoman et al. | 606/64 |
| 5,665,087 A | 9/1997 | Huebner | 606/65 |
| 5,665,089 A | 9/1997 | Dall et al. | |
| 5,669,915 A | 9/1997 | Caspar et al. | |
| 5,676,667 A | 10/1997 | Hausman | |
| 5,709,682 A | 1/1998 | Medoff | 606/60 |
| 5,709,686 A | 1/1998 | Talos et al. | |
| 5,718,705 A | 2/1998 | Sammarco | 606/69 |
| 5,728,099 A | 3/1998 | Tellman et al. | 606/65 |
| 5,733,287 A | 3/1998 | Tepic et al. | |
| 5,749,872 A | 5/1998 | Kyle et al. | |
| 5,766,174 A | 6/1998 | Perry | 606/62 |
| 5,772,662 A | 6/1998 | Chapman et al. | |
| 5,776,194 A | 7/1998 | Mikol et al. | 623/16 |
| 5,785,711 A | 7/1998 | Errico et al. | |
| 5,807,396 A | 9/1998 | Raveh | |
| 5,851,207 A | 12/1998 | Cesarone | |
| 5,853,413 A | 12/1998 | Carter et al. | |
| 5,879,350 A | 3/1999 | Sherman | |
| 5,931,839 A | 8/1999 | Medoff | 606/69 |
| 5,935,128 A | 8/1999 | Carter et al. | |
| 5,938,664 A | 8/1999 | Winquist et al. | |
| 5,941,878 A | 8/1999 | Medoff | |
| 5,951,557 A | 9/1999 | Luter | |
| 5,954,722 A | 9/1999 | Bono | |
| 5,964,763 A | 10/1999 | Incavo | |
| 5,967,046 A | 10/1999 | Muller | |
| 5,968,046 A | 10/1999 | Castleman | |
| 5,968,047 A | 10/1999 | Reed | |
| 5,989,254 A | 11/1999 | Katz | |
| 6,007,535 A | 12/1999 | Rayhack et al. | |
| 6,010,503 A | 1/2000 | Richelsoph | |
| 6,010,505 A | 1/2000 | Asche et al. | |
| 6,022,350 A | 2/2000 | Ganem | |
| 6,053,917 A | 4/2000 | Sherman | |
| 6,096,040 A | 8/2000 | Esser | |
| 6,123,709 A | 9/2000 | Jones | |
| 6,129,730 A | 10/2000 | Bono et al. | |
| 6,146,384 A | 11/2000 | Lee et al. | 606/73 |
| 6,152,927 A | 11/2000 | Farris et al. | |
| 6,183,475 B1 | 2/2001 | Lester et al. | |
| 6,197,028 B1 | 3/2001 | Ray et al. | |
| 6,206,881 B1 | 3/2001 | Frigg et al. | |
| 6,221,073 B1 | 4/2001 | Weiss et al. | |
| D443,060 S | 5/2001 | Benirschke et al. | |
| 6,228,285 B1 | 5/2001 | Wang et al. | |
| 6,231,576 B1 | 5/2001 | Frigg et al. | |
| 6,235,033 B1 | 5/2001 | Brace et al. | |
| 6,235,034 B1 | 5/2001 | Bray | |
| 6,238,395 B1 | 5/2001 | Bonutti | 606/60 |
| 6,241,736 B1 | 6/2001 | Sater et al. | |
| 6,248,109 B1 * | 6/2001 | Stoffella | 606/75 |
| 6,258,089 B1 | 7/2001 | Campbell et al. | |
| 6,270,499 B1 * | 8/2001 | Leu et al. | 606/64 |
| 6,283,969 B1 | 9/2001 | Grusin et al. | |
| 6,290,703 B1 | 9/2001 | Ganem | |
| 6,322,562 B1 | 11/2001 | Wolter | |
| 6,355,041 B1 | 3/2002 | Martin | |
| 6,355,043 B1 | 3/2002 | Adam | |
| 6,358,250 B1 | 3/2002 | Orbay | |
| 6,364,882 B1 | 4/2002 | Orbay | |
| 6,379,359 B1 * | 4/2002 | Dahners | 606/62 |

| | | |
|---|---|---|
| 6,383,186 B1 | 5/2002 | Michelson |
| 6,409,768 B1 | 6/2002 | Tepic et al. |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,468,278 B1 | 10/2002 | Muckter |
| 6,508,819 B1 | 1/2003 | Orbay |
| 6,527,775 B1 * | 3/2003 | Warburton ............... 606/62 |
| 6,540,748 B2 | 4/2003 | Lombardo |
| 6,595,993 B2 | 7/2003 | Donno et al. |
| 6,599,290 B2 | 7/2003 | Bailey et al. |
| 6,602,255 B1 | 8/2003 | Campbell et al. |
| 6,623,486 B1 | 9/2003 | Weaver et al. |
| 6,626,908 B2 | 9/2003 | Cooper et al. |
| 6,645,212 B2 | 11/2003 | Goldhahn et al. |
| 6,669,700 B1 | 12/2003 | Farris et al. |
| 6,679,883 B2 | 1/2004 | Hawkes et al. |
| 6,692,503 B2 | 2/2004 | Foley |
| 6,706,046 B2 | 3/2004 | Orbay et al. ............... 606/69 |
| 6,712,820 B2 | 3/2004 | Orbay |
| 6,719,758 B2 | 4/2004 | Beger et al. |
| 6,730,090 B2 | 5/2004 | Orbay et al. ............... 606/60 |
| 6,730,091 B1 | 5/2004 | Pfefferle et al. |
| 6,755,831 B2 | 6/2004 | Putnam |
| 6,761,719 B2 | 7/2004 | Justis et al. |
| 6,767,351 B2 | 7/2004 | Orbay et al. |
| 6,780,186 B2 | 8/2004 | Errico et al. |
| 6,866,665 B2 | 3/2005 | Orbay |
| 6,926,720 B2 | 8/2005 | Castaneda |
| 6,955,677 B2 | 10/2005 | Dahners |
| 6,974,461 B1 | 12/2005 | Wolter |
| 7,090,676 B2 | 8/2006 | Huebner et al. |
| 7,153,309 B2 | 12/2006 | Huebner et al. |
| 2001/0001119 A1 | 5/2001 | Lombardo |
| 2001/0011172 A1 | 8/2001 | Orbay et al. ............... 606/69 |
| 2001/0021851 A1 | 9/2001 | Eberlein et al. |
| 2002/0032446 A1 | 3/2002 | Orbay |
| 2002/0049445 A1 | 4/2002 | Hall, IV et al. ............... 606/69 |
| 2002/0058939 A1 | 5/2002 | Wagner et al. |
| 2002/0111629 A1 | 8/2002 | Phillips |
| 2002/0147452 A1 | 10/2002 | Medoff et al. |
| 2002/0151899 A1 | 10/2002 | Bailey et al. |
| 2002/0156474 A1 | 10/2002 | Wack et al. |
| 2003/0045880 A1 | 3/2003 | Michelson |
| 2003/0078583 A1 | 4/2003 | Biedermann et al. |
| 2003/0083661 A1 | 5/2003 | Orbay et al. |
| 2003/0105461 A1 | 6/2003 | Putnam ............... 606/69 |
| 2003/0135212 A1 | 7/2003 | Chow |
| 2003/0153919 A1 | 8/2003 | Harris |
| 2003/0216735 A1 | 11/2003 | Altarac et al. |
| 2004/0059334 A1 | 3/2004 | Weaver et al. |
| 2004/0059335 A1 | 3/2004 | Weaver et al. |
| 2004/0068319 A1 | 4/2004 | Cordaro |
| 2004/0073218 A1 | 4/2004 | Dahners |
| 2004/0092935 A1 * | 5/2004 | Manderson ............... 606/69 |
| 2004/0097934 A1 | 5/2004 | Farris et al. |
| 2004/0102778 A1 | 5/2004 | Huebner et al. |
| 2004/0111090 A1 | 6/2004 | Dahners |
| 2004/0193163 A1 | 9/2004 | Orbay |
| 2004/0260291 A1 | 12/2004 | Jensen |
| 2005/0004574 A1 | 1/2005 | Muckter |
| 2005/0080421 A1 | 4/2005 | Weaver et al. |
| 2005/0131413 A1 | 6/2005 | O'Driscoll et al. |
| 2005/0154392 A1 | 7/2005 | Medoff et al. |
| 2005/0165400 A1 | 7/2005 | Fernandez |
| 2005/0187551 A1 | 8/2005 | Orbay et al. |
| 2006/0004462 A1 | 1/2006 | Gupta |
| 2006/0009771 A1 | 1/2006 | Orbay |
| 2006/0015101 A1 | 1/2006 | Warburton et al. |

FOREIGN PATENT DOCUMENTS

| | | |
|---|---|---|
| CH | 675 531 | 10/1990 |
| CN | 1379642 A | 11/2002 |
| DE | 33 01 298 | 2/1984 |
| DE | 40 04 941 | 8/1990 |
| DE | 195 42 116 A | 5/1997 |
| DE | 196 29 011 | 1/1998 |
| DE | 93 21 544 U1 | 9/1999 |
| DE | 43 43 117 C2 | 11/1999 |
| DE | 20200705 | 3/2002 |
| EP | 0 451 427 A1 | 5/1990 |
| EP | 0689800 | 1/1996 |
| EP | 1086655 | 3/2001 |
| EP | 1250892 | 10/2002 |
| FR | 2233973 | 1/1975 |
| FR | 2405062 | 5/1979 |
| FR | 2855391 | 12/2004 |
| JP | 7-10734 | 3/1995 |
| JP | 11-47170 | 2/1999 |
| WO | WO 97/47251 | 12/1997 |
| WO | WO 00/04836 | 2/2000 |
| WO | WO 00/36984 | 6/2000 |
| WO | WO00/66011 | 11/2000 |
| WO | WO01/12081 | 2/2001 |
| WO | WO 01/19267 A | 3/2001 |
| WO | WO01/56452 | 8/2001 |
| WO | WO 2004/032751 | 4/2004 |
| WO | WO 2004/096067 | 11/2004 |

OTHER PUBLICATIONS

"Numelock II Polyaxial Locking System," Stryker Corporation, brochure.

"SCS.TM./D Distal Radius Plate System: Dorsal", Avanta 1997.

"SCS.TM./V Distal Radius Plate: Volar", Avanta 1998.

"SMARTLock Locking Screw Technology," Stryker Corporation, website description, 2004, www.stryker.lcom.

"Summary of Safety and Effectiveness Information"; Synthes.RTM.; Jul. 29, 1998.

"The Distal Radius Plate Instrument and Implant Set", Technique Guide, SYNTHES.RTM., Paoli, PA 1995.

"The Titanium Distal Radius Plate", Technique Guide, SYNTHES.RTM., Paoli, PA, 1995.

"Universal Distal Radius System", Stryker Corporation, website description, 2004, www.stryker.com.

"VAL Plate (Volar Angle Locking) for Distal Radius Fractures", US Implants, brochure.

"Volar Peg Plate Insertion Technique", Trimed, Inc., brochure.

"Volar Radius Plate with Angular Stability", I.T.S. (Implant Technology Systems), 510(k) Summary of Safety and Effectiveness, Feb. 6, 2004.

"Volare Winkelstabile Radiusplatte", I.T.S. (Implant Technology Systems), Spectromed, brochure, 2005, Austria.

Moftakhar, Roham, M.D. and Trost, Gregory R., M.D., "Anterior Cervical Plates: A Historical Perspective", Jan. 2004, pp. 1-5.

Nelson, "Volar Plating with Anatomic Placement and Fixed-Angle Screws", Quick Reference Guide for Contours VPS Volar Plate System by Orthofix, May 2005, www.orthofix.com.

Polyaxial and Monoaxial Spinal Screws, XIA.TM. Spinal System, www.osteonics.com/osteonics/spine/xia2.html, Jun. 25, 2002.

Putnam, D. M.D., "Repair and Rehabilitation of Distal Fractures: The Role of Ssubchondral Fixation" at pp. 144-147.

* cited by examiner

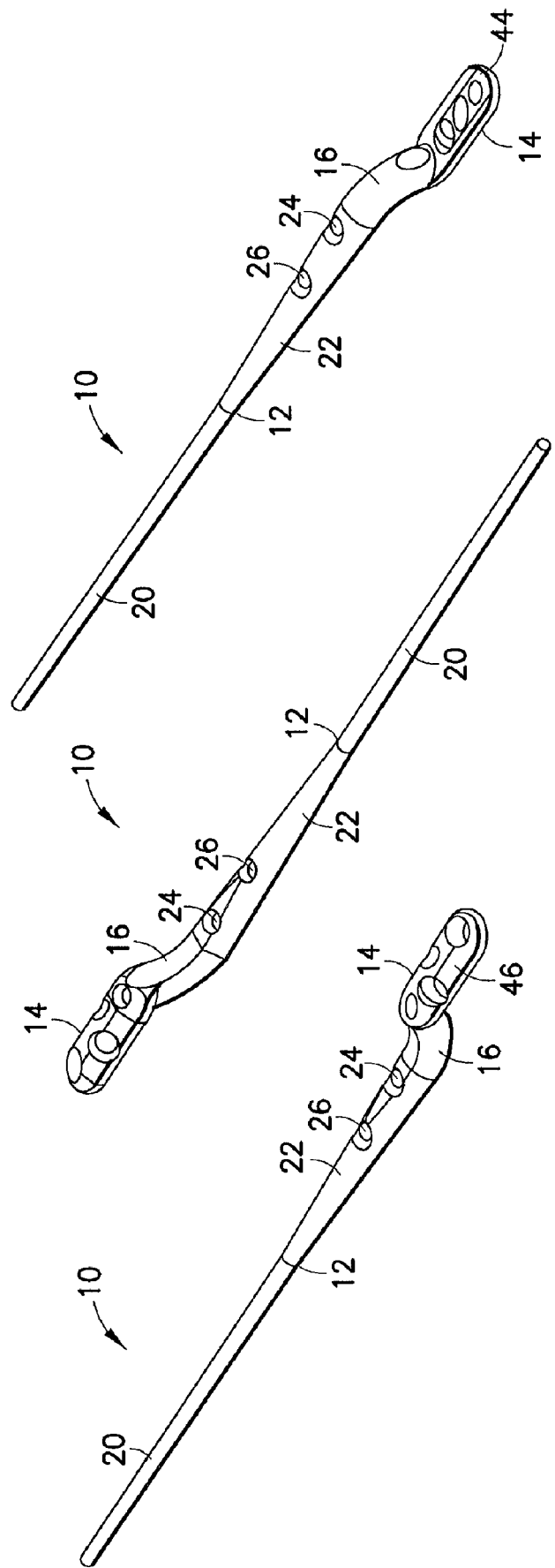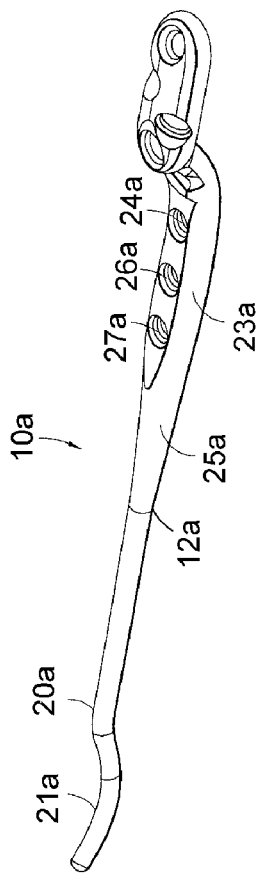

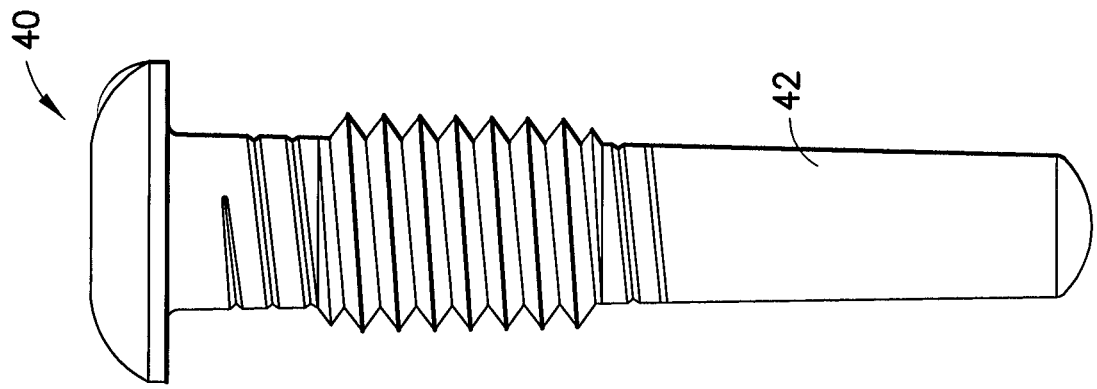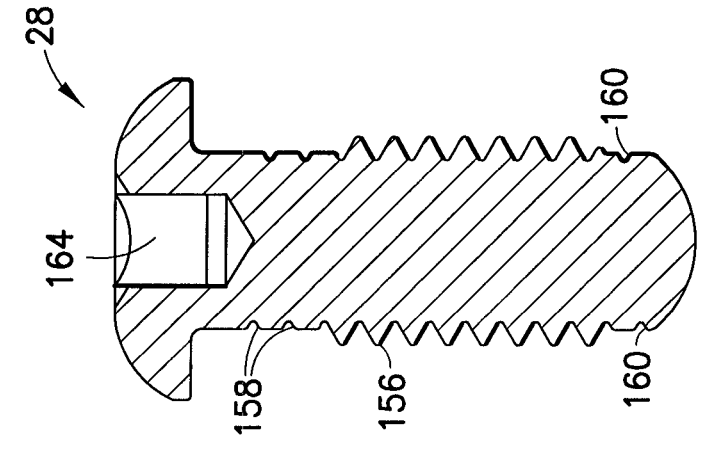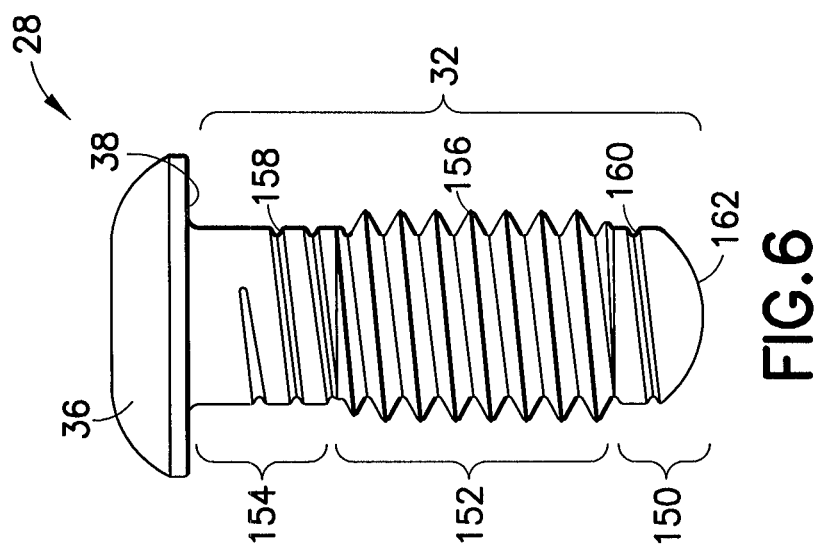

INTRAMEDULLARY FIXATION DEVICE FOR METAPHYSEAL LONG BONE FRACTURES

RELATED APPLICATIONS

This application claims priority under 35 U.S.C. §371 to PCT/US03//14775, filed May 9, 2003, which is a continuation-in-part of U.S. Ser. No. 10/315,787, filed Dec. 10, 2002, now issued as U.S. Pat. No. 6,706,046, which is a continuation-in-part of U.S. Ser. No. 10/159,611, filed May 30, 2002, now issued as U.S. Pat. No. 6,730,090.

BACKGROUND OF THE INVENTION

1. Field of the Invention

This invention relates broadly to surgical devices. More particularly, this invention relates to cross-fastened intramedullary implants for the fixation of bone fractures.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis, and may require extensive periosteal stripping in order to apply the plate on the bone surface. As such, many of the less displaced fractures, and particularly metaphyseal fractures (fractures at the end of the long bones), remain undertreated.

By way of example, a Colles' fracture, which results from compressive forces being placed on the distal radius bone, and which causes backward displacement of the distal fragment and radial deviation of the hand at the wrist, is treated with a dorsal plate when there is a significant degree of displacement. However, a less-displaced Colles' fracture is commonly undertreated due to the hesitancy of physicians to prescribe operative and invasive treatment. If not properly treated, such a fracture results in permanent wrist deformity. It is therefore important to align the fracture and fixate the bones relative to each other so that proper healing may occur.

In addition, there is no relatively minimally invasive procedure to treat fractures occurring at the metaphysis and that also provides the desired reduction and immobilization for such fractures.

Furthermore, there is no relatively minimally invasive procedure to treat distal radius fractures that provides the stability generally obtained by more invasive procedures, such as open reduction and internal fixation.

SUMMARY OF THE INVENTION

It is therefore an object of the invention to provide a relatively minimally invasive treatment which provides stabilization and support to long bone fractures.

It is another object of the invention to provide a relatively minimally invasive treatment which provides stabilization and support to metaphyseal fractures.

It is a further object of the invention to provide a implant which is fixedly held within the medullary canal of a long bone.

In accord with these objects, which will be discussed in detail below, a fixation system includes a device having a proximal nail portion and a distal plate portion, preferably horizontally and vertically offset relative to the nail portion by a neck portion. The nail portion includes a tapered end which is resilient, and a relatively rigid distal portion larger in diameter. For treatment of distal radius fractures, the distal portion of the nail portion preferably includes two threaded screw holes, and the plate portion has a low, narrow profile and includes three longitudinally displaced peg holes, each of which is adapted to orient a peg in a different orientation from the others. The plate portion also includes a threaded guide hole at which a guide can be stabilized with a screw in order to drill holes in alignment with the screw holes and pegs holes. The system also includes unicortical machine screws having a reasonably large head adapted to seat against the outer surface of the bone and a threaded shaft adapted to engage in the screw holes, and pegs adapted to engage in the peg holes.

In use, a relatively small incision is made in the skin, and the tapered end of the nail portion of the device is introduced percutaneously through the incision and through the fracture location into the medullary canal of the bone. The plate portion of the device is then maneuvered against a surface of the bone. The guide is coupled to the guide hole and the screw holes and peg holes are drilled. It is noted that the screw holes need only be drilled through the near side of the cortical bone, and not through the nail portion or the far side of the cortical bone.

The unicortical screws are then introduced through drilled holes and into the screw holes in the nail portion. The screws are tightened to pull the nail portion against the inner surface of the cortical bone. As the screws are tightened, the nail portion is pulled against the inner cortex and is automatically aligned with the axis of the bone. Thus, the plate portion is also thereby provided in a proper orientation for support of the metaphyseal area. In addition, as the screw heads are relative large, the bone is clamped between the screw heads and the nail portion. As a result, stability is increased. Alternatively, a combination of unicortical screws and bicortical screws can be used through the cortical screw holes.

The fracture at the metaphyseal portion of the bone is then reduced, and pegs are introduced through the drilled holes until the heads of the peg thread into the peg holes of the plate portion of the device. The pegs provide stabilization and support for subchondral fragments. Moreover, as the pegs preferably enter the subchondral fragments from a plurality of directions, additional fixation of the device into the bone is provided.

The fixation system permits a minimally invasive treatment of long bone fractures that may otherwise be undertreated. In addition, such fixation is very stable due to the clamping of the bone between the large screw heads and the device. Moreover, the large screw heads distribute the stress on the bone over a relatively large surface area on the outer surface of the cortical bone. The fixation system can be adapted to treatment of fractures at multiple sites. For example, the distal radius, the proximal humerus, the distal femur, the proximal tibia, the distal tibia, and the hip are all suitable for application of the system of the invention.

Additional objects and advantages of the invention will become apparent to those skilled in the art upon reference to the detailed description taken in conjunction with the provided figures.

BRIEF DESCRIPTION OF THE DRAWINGS

FIG. 1 is a distal end top perspective view of the fixation device of the invention;

FIG. 2 is a proximal end top perspective view of the fixation device of the invention;

FIG. 3 is a distal end bottom perspective view of the fixation device of the invention;

FIG. 6 is a side view of a unicortical machine screw in accord with the system of the invention;

FIG. 6A is a longitudinal section view of the unicortical screw of FIG. 6;

FIG. 7 is a side view of a bicortical machine screw in accord with the system of the invention;

FIG. 17 is a distal end top perspective view of an alternate embodiment of the fixation device of the invention.

DETAILED DESCRIPTION OF THE PREFERRED EMBODIMENTS

Turning now to FIGS. 1 through 5, a fixation device 10 for the treatment of a fracture at an end of a long bone, i.e., a metaphyseal fracture, is provided. The device 10 is preferably made of metal, e.g., titanium or stainless steel, and includes an intramedullary nail portion 12 and a plate portion 14 that is preferably horizontally and vertically offset relative to the nail portion at a neck portion (or transition zone) 16. As such, the nail portion 12 and the plate portion 14 are fixed in a parallel, but non-coaxial relationship, with the plate portion 14 longitudinally displaced relative to the nail portion 12.

Figure 4:
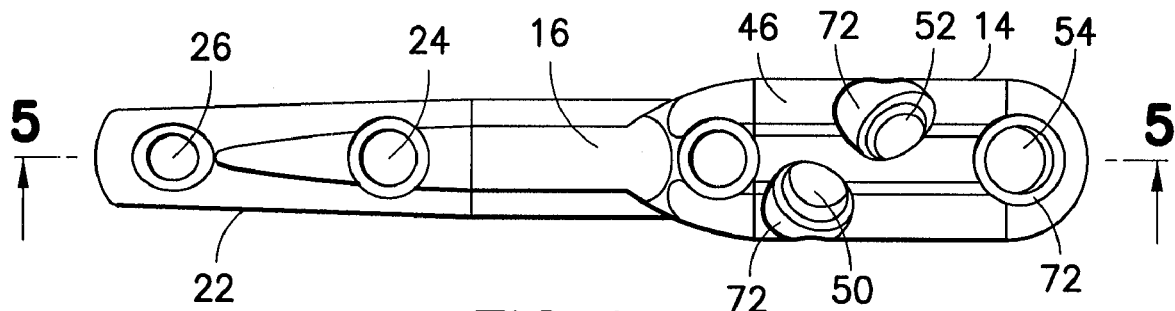
FIG. 4 is a broken top view of the fixation device of the invention.
Figure 5:
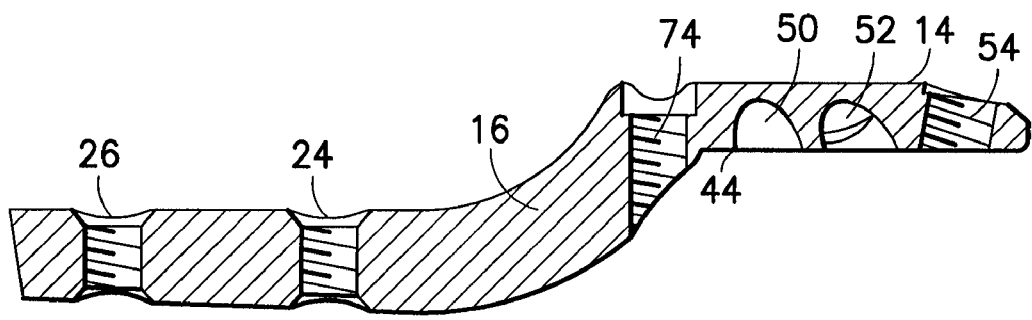
FIG. 5 is a broken longitudinal section view taken along line 5-5 in FIG. 4.
Figure 10:
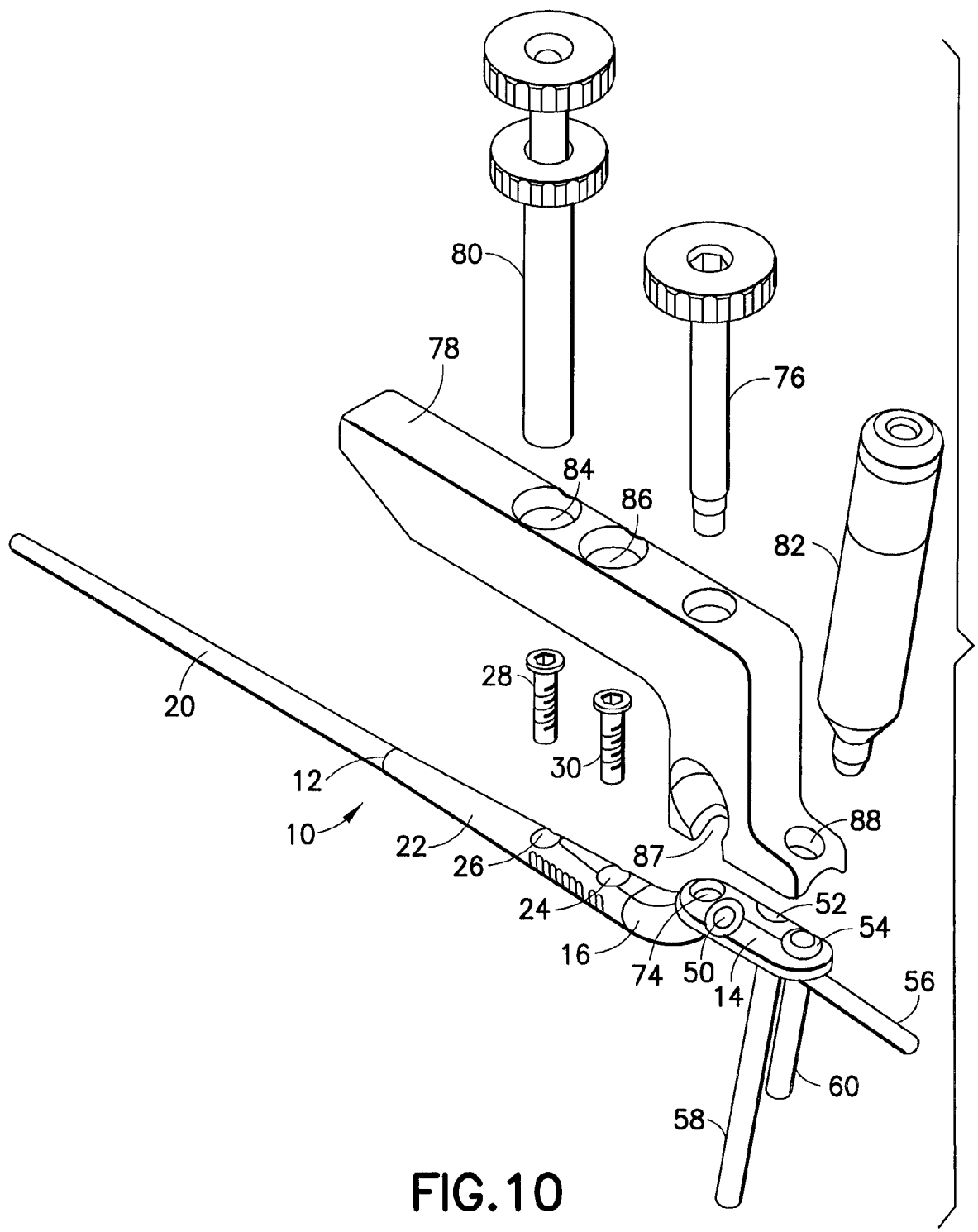
FIG. 10 is an exploded perspective view of the system of the invention in combination with a jig and drill guides.

The nail portion 12 is preferably substantially circular in cross section and includes a tapered resilient (flexible) section 20, and a relatively rigid section 22 generally substantially larger in diameter adjacent the shoulder portion 16. The resilient section 20 may be straight, or referring to FIG. 17 which shows an alternate embodiment of the fixation device 10a, the resilient section 20a may include a curved section 21a to facilitate introduction of the nail portion 12a into the medullary canal of the bone. If the curved section 21a is provided, the curve preferably extends within a plane extending through the longitudinal axes of the both the nail portion 12 and the plate portion 14. The rigid section 22 preferably either tapers toward and into the resilient section 20 (FIGS. 1 through 3), or includes a constant diameter portion 23a and a tapered portion 25a (FIG. 17). Referring to FIGS. 4 and 5, the rigid section 22 of the nail portion 12 preferably includes two threaded screw holes 24, 26 preferably extending vertically through the diameter of the nail portion 12 and longitudinally displaced along the length of the rigid section 22. Referring again to FIG. 17, three screw holes 24a, 26a, 27a, and thus it is appreciated that additional screw holes may be provided to the device. The screw holes 24, 26 are adapted to receive machine screws 28, 30 (FIG. 10). In an alternate embodiment, the screw holes 24, 26 may be non-threaded and, as such, adapted to receive bicortical bone screws.

Referring to FIGS. 6, 6A and 10, the machine screws 28, 30 are preferably unicortical in design. That is, the shaft 32 of each screw is selected in length (for the particular bone being treated) to extend through a near cortex of the bone and to thread into the screw holes 24, 26 of the nail portion 12, but preferably not to extend to the far cortex of the bone. The shaft 32 includes a tip portion 150, a body portion 152, and clearance portion 154. The body portion 152 includes threads 156 adapted to engage in the screw holes 24, 26. In the clearance portion 154, the shaft is relatively smooth, but has a shallow thread channel 158 extending therein which is continuous with and the same pitch as threads 156. The thread channel 158 is sized to accommodate the threads in screw holes 24, 26. The tip portion 150 is preferably also relatively smooth, but slightly smaller in diameter than the clearance portion 154; e.g., a 0.098 inch diameter at the clearance portion 154 versus a 0.095 inch diameter at the tip portion 150. In addition, the tip portion 150 preferably also has a shallow thread channel 160 extending therein which is continuous with and the same pitch as threads 156. The tip portion 150 preferably also has a relatively blunt end 162, as the screw is not intended to tap into bone. In addition, each screw 28 has a reasonably large head 36 with a substantially flat undersurface 38 adapted to contact bone and distribute load and stress, and a driver receiving slot 164.

As an alternative to providing solely unicortical screws 28, a combination of unicortical screws 28 and relatively longer bicortical screws 40, which preferably have a relatively long tip portion 42 adapted to extend to or even into the far cortex, can be used (FIG. 7).

Referring back to FIGS. 1 through 5, the plate portion 14 is substantially rigid and has a low and narrow profile. The plate portion 14 is less than one half the length of the nail portion 12, has a thickness less than a maximum diameter of the nail portion, and a width greater than the maximum diameter of the nail portion. The plate portion 14 has a slightly concave bottom surface 44 (adapting the plate portion to the anatomy) and a slightly convex upper surface 46 (reducing potential irritation of tendons and other tissue). The concave and convex surfaces 44 and 46 may be defined by facets approximating curved surfaces. The plate portion 14 also includes preferably three longitudinally displaced, threaded peg holes 50, 52, 54, each of which is preferably adapted to orient a respective peg 56, 58, 60 (FIGS. 8 and 10) in a different orientation from the others; i.e., the axes of the peg holes are oblique relative to each other. The threads of the peg holes 50, 52, 54 may be of a different pitch than the threads in screw holes 24, 26; the pitches or each are independent.

Figure 8:
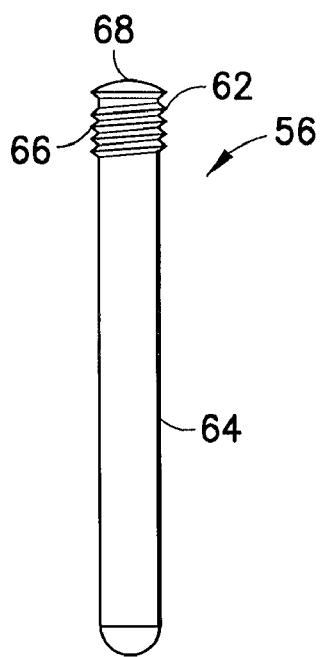
FIG. 8 is a side view of a fixed-angle peg in accord with the system of the invention.
Figure 9:
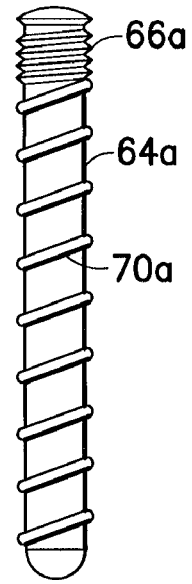
FIG. 9 is a side view of an alternative threaded fixed-angle peg in accord with the system of the invention.

Referring to FIG. 8, each peg, e.g., peg 56, includes a head 62 and a shaft 64. The head 62 has external threads 66 adapted to engage within the threaded peg holes 50, 52, 54, and a slot 68 for receiving a driver. Thus, the head 62 of the peg 56 (unlike typical screws) is adapted to threadably engage in a respective peg hole generally only in alignment with the axis through the respective peg hole. Thus, such peg systems are often referred to as 'fixed angle' devices. The shaft 64 is preferably smaller in diameter than the head 62, and also preferably non-threaded. However, referring to FIG. 9, the shaft 64a may optionally be provided with threads 70a. Such threads on the shaft are preferably of a different pitch than the threads 66a about the head of the peg. As another alternative, multidirectional pegs (which may be angled relative to the peg hole axis and then secured in the peg hole in the desired direction) and peg holes adapted therefor can also be used, as described in co-owned and co-pending U.S. Ser. No. 10/307,796, filed Dec. 2, 2002, which is hereby incorporated by reference herein in its entirety.

Referring to FIGS. 4, 5, and 10, in a preferred embodiment for a left-hand device 10, peg hole 50 is adapted to orient a first peg 56 approximately 41° laterally and approximately 25° relative to a line normal to the lower surface 44 of the plate portion 14 in a direction away from the nail portion 12; peg hole 52 is adapted to orient a second peg 58 approximately 41° laterally (in a direction opposite first peg 40) and approximately 15° relative to a line normal to the lower surface 44 of the plate portion 14 in a direction away from the nail portion 12; and peg hole 54 is adapted to orient a third peg 60 in the plane of the plate and nail portions 12, 14 and approximately 10° toward the nail portion 12. It is appreciated that the lateral angles are preferably opposite for a right-hand device. It is preferable that the laterally extending first and second pegs 56, 58 be substantially longer than the distal third peg 60. In alternate arrangement, the peg holes and pegs can be provided in a fanned arrangement or otherwise, particularly where one or more multidirectional pegs, as described in previously incorporated co-pending U.S. Ser. No. 10/307,796, are used. In addition, the peg holes 50, 52, 54 preferably each include a countersink portion 72 adapted to permit the heads 62 of the pegs to be at least partially countersunk into the plate portion 14, so as to provide a relatively smooth profile to the plate portion.

The plate portion 14 also includes a screw hole 74 adjacent the neck portion 16 that is adapted to receive a jig screw 76 which couples a drill guide jig 78 (FIG. 10) over the device 10. Drill guides 80, 82 can be used through guide holes 84, 86, 87, 88 in the guide jig 78 to drill holes, from outside the bone, through the bone and in alignment with the screw holes 22, 24 and the peg holes 50, 52, 54.

Figure 11:
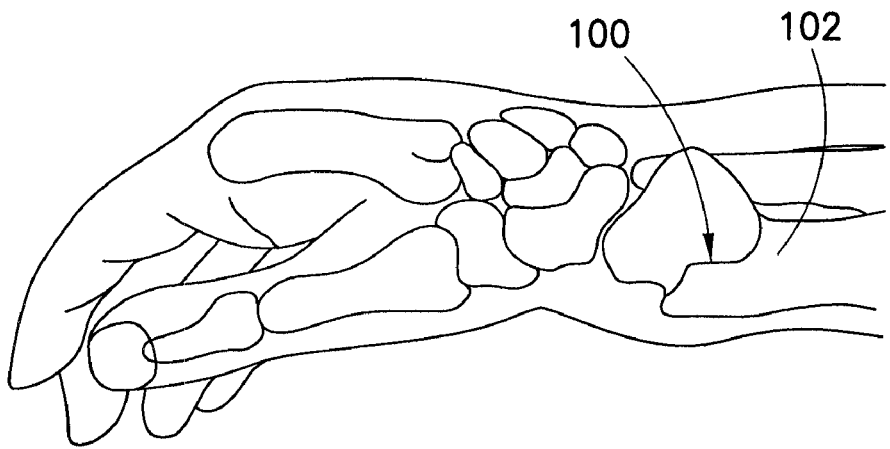
FIGS. 11 through 16 illustrate a method of using the fixation system of the invention to stabilize a fracture.
Figure 12:
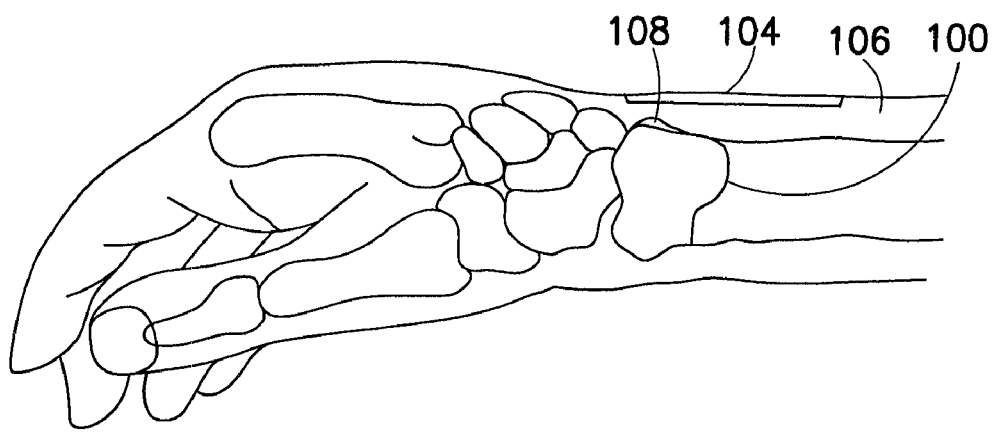
Figure 13:
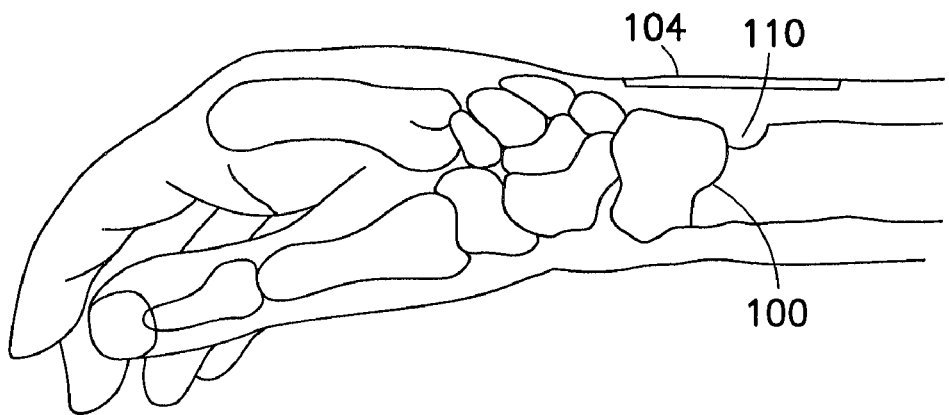

The device 10 is used as follows to treat a fracture 100 of the distal radial bone 102 (e.g., a Colles' fracture), as represented in FIG. 11. Referring to FIG. 12, first, a relatively small incision 104 (generally approximately 4 cm in length) is made in the skin 106 on the dorsal side of the fracture 100. For distal radial fractures, the incision is preferably at a location between the second and third extensor compartments and above Lister's tubercule 108 (a small bump a the distal end of the radius bone) so that the extensor tendons are not irritated by the incision or by the implanted device 10. Referring to FIG. 13, a rongeur (not shown) is then used to take small bites out of the bone at the broken end of the radius bone so that a notch 110 is created preferably on the proximal side of the distal radius fracture 100. In addition, at least a portion of Lister's tubercule is preferably removed to provide a surface for placement of the plate portion 14 at a location which will not cause tendon irritation.

Figure 14:
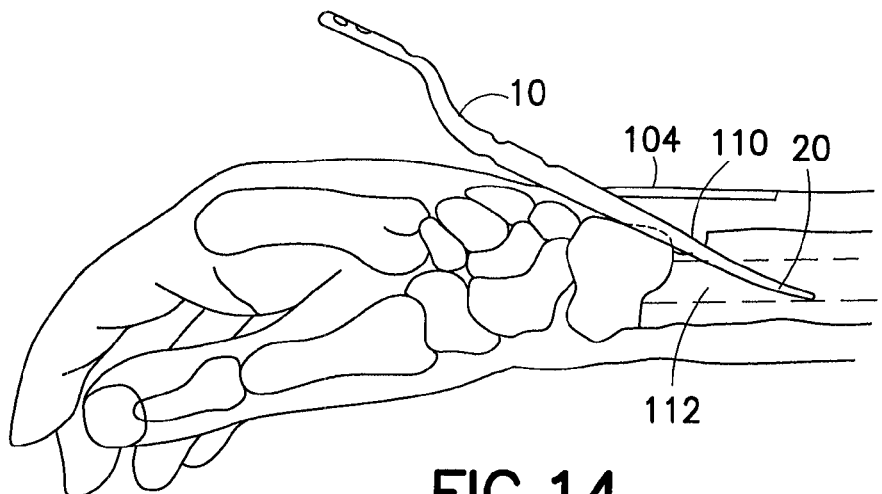

Referring to FIG. 14, the tapered resilient section 20 of the nail portion 12 of the device is then introduced percutaneously (via incision 104) through the notch 110 and into the medullary canal 112 of the bone. The nail portion 12 is pushed into the medullary canal 112 of the radius bone 102 until the neck portion 16 lies in the notch 110 created in the distal end of the bone and the plate portion 14 is positioned on the bone distal of the fracture and at the surface of the removed portion of Lister's tubercule. It is appreciated that reduction of the fracture (from the bone position of FIG. 11 to the bone position of FIGS. 12 through 15) may occur at this stage or at any other medically reasonable time during the fracture fixation process. During introduction into the bone and when implanted in the bone, the resilient section 20 is permitted to undergo some degree of bending, which may be necessitated if the entryway into the bone for the nail portion is too small of if the medullary canal is not be perfectly straight.

Figure 15:
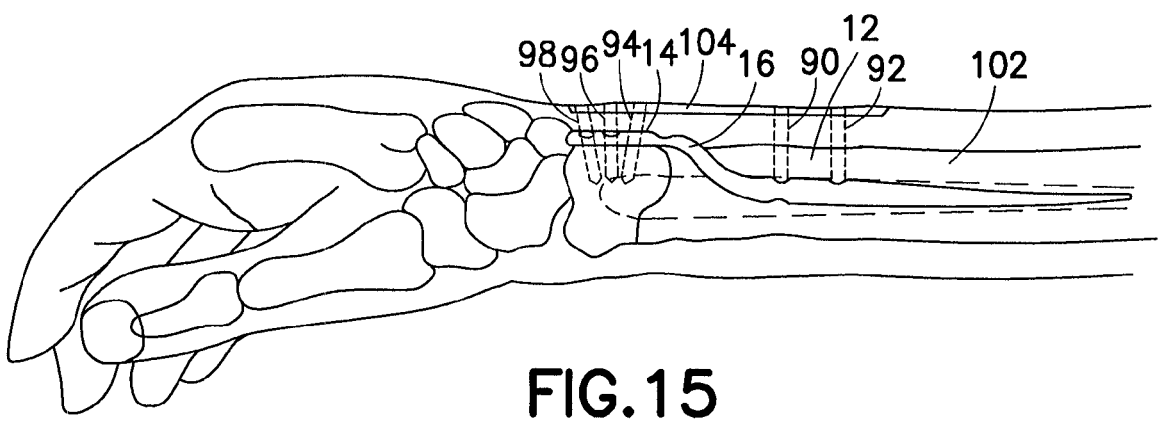

Referring to FIGS. 10 and 15, the jig 78 is then fixed to the device 10 at hole 74 with the guide screw 76, and the guides 80 and 82 are placed in the jig 78. The tissue (e.g., the muscle tissue and periosteum) over the bone and beneath the guide holes 84, 86 is relocated. Using a drill, holes 90, 92 are drilled through the guide 80 (which is positioned in each of guide holes 84 and 86) and into the near cortical bone into alignment with the screw holes 24, 26. In addition, holes 94, 96, 98 are drilled through guide 82 (which is positioned in each of guide holes 87, 88 (not shown), 89 in alignment with each of peg holes 50, 52, 54) and into the subchondral bone.

Figure 16:
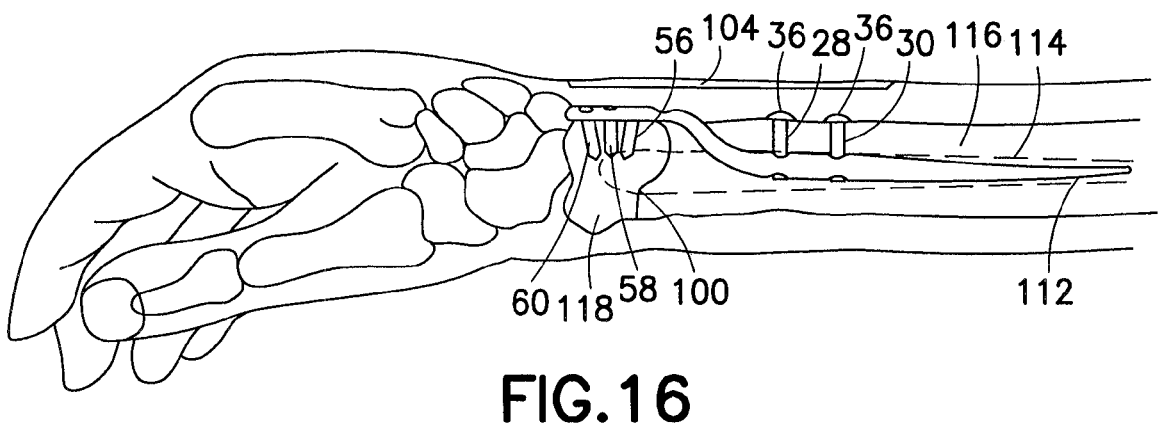

Referring to FIGS. 6, 6A and 16, the unicortical screws 28, 30 are then introduced through the drilled holes 90, 92 and into the screw holes 24, 26 in the nail portion 12. The distal-most screw 28 is preferably inserted first into screw hole 24 and tightened. The threaded channel 160 self-aligns the screw 28 in the screw hole 24 to prevent cross-threading. The body portion 152 of the screw 28 engages the screw hole 24, and the clearance portion 154 permits free rotation inside the cortical wall 116. Thus, as the screw 28 is rotated, the rigid portion 22 of the nail portion 12 functions as nut for the screw 28 and is pulled up against the interior surface 114 of the cortical bone. The thread channel 158 of the clearance portion 154 permits engagement of the rigid portion 22 of the nail portion 12 over a large range of cortical bone wall thicknesses. Thus, if the bone wall is thinner than the length of the clearance portion, the screw 28 can be further inserted which engagement is maintained between the screw and the screw hole. Then, the relatively proximal screw 30 is similarly inserted into the respective screw hole 26 and tightened. Tightening of both screws 28, 30 operates to pull the rigid portion 22 of the nail portion 12 against the inner surface 114 of the cortical bone 116 and into a desired alignment with respect to the medullary canal 112 of the bone. Moreover, due to the taper along the rigid portion 22 of the nail portion 12, upon tightening of the screws 28, 30, the entire device 10 is oriented in a slightly palmar direction such that the plate 14 is forced against the subchondral fragments 118 to facilitate reduction and stabilization of the fracture 100. Thus, the plate portion 14 is also thereby provided into a proper orientation for support of the metaphyseal area. In addition, as the screw heads 36 are relative large, the bone 116 is clamped between the screw heads 36 and the rigid section 22 of the nail portion 12, and stability of the device is increased. Alternatively, a combination of unicortical screws 28 and bicortical screws 40 (FIG. 7) can be used through respective screw holes such that the device is stably held. If bicortical screws are used, the tip thereof may be extended through a hole drilled in the far cortex, or the tip may extend to contact the inner surface of the far cortex.

The pegs 56, 58, 60 are then introduced through drilled holes 94, 96, 98 until the heads 66 of the pegs thread into the peg holes 50, 52, 54 of the plate portion 14 of the device 10. The pegs 56, 58, 60 provide stabilization and support for subchondral fragments, including the radial styloid and the volar dipunch. Moreover, the pegs preferably enter the subchondral fragments from a plurality of directions, providing additional fixation of the device 10 to the bone.

The fixation system permits a relatively minimally invasive treatment of long bone fractures that may otherwise be under-treated. In addition, such fixation is very stable due to the clamping of the bone between the large screw heads and the device. Moreover, the large screw heads distribute the stress on the bone over a relatively large surface area on the outer surface of the cortical bone.

When the device is used to treat a distal radial fracture, such as a Colles' fracture, particular dimensions are preferred, though the dimensions of the device are not limited thereto. Such preferred dimensions include an overall device length of approximately 4.2 inches, with the nail portion having a length of approximately 3.56 inches, and the plate portion having a length of approximately 0.65 inch. The bottom surface of the plate portion is preferably located approximately 0.29 inch above a longitudinal axis extending through the nail portion. The preferred length for the unicortical screws is preferably approximately 0.28 inch (under the head), and the length of the bicortical screws is preferably approximately 0.60 inch (under the head). The laterally extending first and second pegs 56, 58 are preferably approximately 1 inch in length, and the distalmost third peg 60 is preferably approximately 0.7 inch in length.

The fixation system can be adapted for treatment of fractures at multiple sites. For example, the distal radius, the proximal humerus, the distal femur, the proximal tibia, the distal tibia, and the hip are all suitable for application of the system of the invention, although the device and screws of the system may need to be dimensioned appropriately for the site of use.

There have been described and illustrated herein embodiments of a fixation device and a method of using the device to treat bone fractures. While particular embodiments of the invention have been described, it is not intended that the invention be limited thereto, as it is intended that the invention be as broad in scope as the art will allow and that the specification be read likewise. Thus, while particular dimensions have been disclosed, it will be appreciated that other dimensions may be used as well. In addition, while titanium and stainless steel are the preferred materials, it will be understood that other biocompatible materials can be used. Moreover, the resilient portion may be made from a different material than the rigid portion and/or the plate portion, and the two portions may then be joined. In addition, particular in application for larger bones, more than two machine screw holes and screws therefor may be used. Also, while three pegs are preferred, one or more pegs may be used, and more than three can be used in relatively larger devices. Furthermore, not all of the peg holes or screw holes need by provided with pegs and screws. However in accord with the invention, it is preferred that at least one peg and at least one screw are used in the fixation system. It will therefore be appreciated by those skilled in the art that yet other modifications could be made to the provided invention without deviating from its spirit and scope as claimed.

What is claimed is:

1. A one-piece bone fracture fixation device for use with a fastener having a head portion with a diameter larger than a shaft portion, said device for stabilization of a fracture of a bone of an upper extremity, the bone having a metaphysis and diaphysis, the diaphysis defining a medullary canal, said device comprising:
   a) an elongate nail portion having a first length and including a first portion with a first diameter with at least one threaded screw hole extending therein and an opposite second portion having a smaller diameter than said first portion and having a decreased rigidity relative to said first portion thereby permitting the second portion to flex relative to the first portion, an entirety of said nail portion sized to be received within the medullary canal of the bone;
   b) a plate portion extending from and inseparable from said nail portion, said plate portion having a second length less than one half said first length and having a maximum thickness less than said first diameter, said plate portion provided adjacent said first portion of said nail portion, said plate portion including at least one hole having a longitudinal axis extending through said hole and a countersink portion configured to allow the head portion of the fastener to be countersunk within the plate portion and to fix the fastener within said hole in a fixed angle orientation along said longitudinal axis; and
   c) a neck region that connects said plate portion to said first portion of said nail and offsets said plate portion from said first portion of said nail portion so that said plate portion is parallel to but not coaxial with said first portion of said nail portion, said neck region including a threaded hole, and
   each of said plate portion and said first portion of said nail portion extend from said neck region in opposite, and not in the same, directions from each other from said neck region.

2. A device according to claim 1, wherein:
said nail portion has a longitudinal axis, and said second portion of said nail terminates in a section that curves relative to said longitudinal axis.

3. A device according to claim 1, wherein:
said device has a longitudinal axis in a direction extending from said nail portion to said plate portion, and said plate portion has an upper surface that is convexly curved in a direction transverse to said longitudinal axis.

4. A device according to claim 3, wherein:
said plate portion has a lower surface that is concavely curved in a direction transverse to said longitudinal axis.

5. A device according to claim 1, wherein:
said device has a longitudinal axis in a direction extending from said nail portion to said plate portion, and said plate portion has a lower surface that is concavely curved in a direction transverse to said longitudinal axis.

6. A device according to claim 1, wherein:
said first portion of said nail includes a plurality of threaded screw holes, all extending through said nail in a parallel orientation, and
said plate portion includes a plurality of screw holes, each configured to guide respective fasteners in a discrete axis such that none of the axes defined by the screw holes in the plate portion are parallel.

7. A device according to claim 1, wherein:
said threaded hole in said neck region is oriented parallel with the at least one threaded screw hole in the first portion of the nail portion.

8. A device according to claim 1, wherein:
said nail portion is divided equally by length into said first and second portions, and said second portion is absent of any screw holes.

9. A device according to claim 1, wherein:
said nail portion includes two threaded screw holes and has a longitudinal axis, and said first portion of said nail is non-circular in cross-section transverse to said longitudinal axis at a location between said two threaded screw holes.

10. A device according to claim 1, wherein:
said nail portion has a longitudinal axis, and said first portion of said nail has a circular cross-section in a direction transverse to said longitudinal axis.

11. A device according to claim 1, wherein:
said nail portion has a longitudinal axis, and said second portion of said nail portion has a round cross-section in a direction transverse to said longitudinal axis.

12. A device according to claim 11, wherein:
said second portion of said nail portion has said round cross-section shape along its entire length.

13. A device according to claim 12, wherein:
said first portion of said nail portion has a round cross-section shape in a direction transverse to said longitudinal axis.

14. A device according to claim 1, wherein:
said nail portion defines a longitudinal axis, and said plate portion includes three holes configured to guide fasteners, each of said holes aligned on said longitudinal axis and configured to orient a fastener in a discrete fixed angle orientation.

15. A device according to claim 14, wherein:
each of said three holes is threaded and adapted to receive a fastener with a threaded head.

16. A one-piece bone fracture fixation device for use with a fastener, said device for stabilization of a fracture of a bone of an upper extremity, the bone having a metaphysis and diaphysis, the diaphysis defining a medullary canal, said device comprising:
   a) an elongate nail portion having a first length and including a first portion with a first diameter with at least one threaded screw hole extending therein and an opposite second portion having a smaller diameter than said first portion and having a decreased rigidity relative to said first portion thereby permitting the second portion to flex relative to the first portion, an entirety of said nail portion sized to be received within the medullary canal of the bone;
   b) a plate portion extending from and inseparable from said nail portion, said plate portion having a second length less than one half said first length and having a maximum thickness less than said first diameter, said plate portion provided adjacent said first portion of said nail portion, said plate portion including at least one hole configured to guide the fastener through said hole in a fixed angle orientation; and
   c) a neck region that connects said plate portion to said first portion of said nail and offsets said plate portion from said first portion of said nail portion so that said plate portion is parallel to but not coaxial with said first portion of said nail portion, said neck region including a threaded hole oriented parallel with the at least one threaded screw hole in the first portion of the nail portion, and
   each of said plate portion and said first portion of said nail portion extend from said neck region in opposite, and not in the same, directions from each other from said neck region.

* * * * *